US009713725B2

(12) United States Patent
Bobgan et al.

(10) Patent No.: US 9,713,725 B2
(45) Date of Patent: Jul. 25, 2017

(54) IMPLANTABLE MEDICAL DEVICES HAVING FLEXIBLE ELECTROMAGNETIC INTERFERENCE AND DUMP RESISTOR SHIELDS

(71) Applicant: CARDIAC PACEMAKERS, INC., St. Paul, MN (US)

(72) Inventors: Jean M. Bobgan, Maple Grove, MN (US); James E. Blood, Shoreview, MN (US); Moira B. Sweeney, St. Paul, MN (US); Ron A. Balczewski, Bloomington, MN (US); William J. Linder, Golden Valley, MN (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 0 days.

(21) Appl. No.: 14/997,758

(22) Filed: Jan. 18, 2016

(65) Prior Publication Data

US 2016/0287865 A1    Oct. 6, 2016

Related U.S. Application Data

(60) Provisional application No. 62/143,463, filed on Apr. 6, 2015.

(51) Int. Cl.
| A61N 1/00 | (2006.01) |
| A61N 1/375 | (2006.01) |
| A61N 1/37 | (2006.01) |
| A61N 1/39 | (2006.01) |

(52) U.S. Cl.
CPC ............ *A61N 1/375* (2013.01); *A61N 1/3718* (2013.01); *A61N 1/3968* (2013.01); *A61N 1/3931* (2013.01); *A61N 1/3956* (2013.01); *H05K 2201/10371* (2013.01)

(58) Field of Classification Search
CPC ...... A61N 1/08; A61N 1/3931; A61N 1/3956; H05K 9/0088; H05K 9/0081
See application file for complete search history.

(56) References Cited

U.S. PATENT DOCUMENTS

| 7,769,457 | B2 | 8/2010 | Fonte | |
| 9,105,899 | B2 * | 8/2015 | Pakula | ................ H01M 2/1022 |
| 2003/0204216 | A1 | 10/2003 | Ries et al. | |
| 2005/0245971 | A1 | 11/2005 | Brockway et al. | |
| 2012/0069536 | A1 | 3/2012 | Sporon-Fiedler | |

* cited by examiner

*Primary Examiner* — Robert N Wieland
(74) *Attorney, Agent, or Firm* — Seager, Tufte & Wickhem LLP

(57) ABSTRACT

Implantable medical devices comprising electromagnetic interference shields which incorporate a dump resistor and various enhancements to control high voltage arcing. Included are embodiments in which a dump resistor is provided in a flexible shield having first and second conductive layers, where the resistor is provided in a layer between the conductive layers. In additional examples the design of plated through-holes is done to avoid the potential for arcing while maintaining close spacing.

20 Claims, 14 Drawing Sheets

IMPLANTABLE MEDICAL DEVICES HAVING FLEXIBLE ELECTROMAGNETIC INTERFERENCE AND DUMP RESISTOR SHIELDS

CROSS REFERENCE TO RELATED APPLICATIONS

The present application claims the benefit of and priority to U.S. Provisional Patent Application Ser. No. 62/143,463, filed Apr. 6, 2015, the disclosure of which is incorporated herein by reference.

FIELD

The present invention relates to the field of implantable medical devices. More particularly, the present invention relates to implantable medical devices that include internal shielding to prevent electromagnetic interference with circuitry contained in such devices.

BACKGROUND

Implantable cardiac stimulus devices, as well as many other implantable medical devices, typically include control circuitry that is adapted to perform various functions such as sensing, communication and/or stimulus delivery. Such devices operate within a patient's body, and are subject to various sources of electromagnetic interference (EMI) including, for example, noise from other electrical devices inside or outside of the patient's body, power line noise, noise generated by the patient's body itself, and, for some devices, noise that the device itself generates. For example, implantable cardiac stimulus devices typically deliver electric pulses to regulate or correct cardiac activity, and their sensing algorithms are often configured to avoid capturing self-generated signals. Some such devices, known as implantable cardioverter defibrillators (ICDs), deliver very large stimuli to shock a patient's heart out of an arrhythmic state such as ventricular tachycardia or ventricular fibrillation. When large pulses are delivered, it is desirable to limit the effects of the large pulse on operation of internal circuitry.

Certain devices must also be configured to dump charge. For example, during implant testing, an ICD may be required to deliver an induction signal to place a patient's heart in a desired arrhythmia (usually ventricular fibrillation), and then to detect and treat the induced arrhythmia. Once the induced arrhythmia is detected, the ICD will prepare for therapy by charging high power capacitors to a desired energy level. If the induced arrhythmia spontaneously terminates, however, for example by reverting to a normal sinus rhythm, the ICD will not deliver the therapy it has prepared itself for, and the induction test will be restarted. Prior to restarting the induction, the ICD must dump the high power capacitors safely. One approach is to use a dump resistor inside the device. The dumping operation must be performed relatively quickly, since the induction test generally takes place in the surgical suite and the patient and physician are both waiting. However, dumping cannot be done in a manner that causes excessive heating of the device, as heating beyond certain limits may be harmful to patients and is not allowed under internationally accepted device safety standards.

New and alternative designs for implantable medical devices are desired, and preferably such devices will address the above design needs.

OVERVIEW

The present inventors have recognized, among other things, that a problem to be solved includes a need for a combined EMI shield and resistor dump component.

The present invention, in an illustrative embodiment, includes an implantable medical device that includes operational circuitry contained in a housing. An EMI shield is disposed between the operational circuitry and the housing. The EMI shield, in an illustrative embodiment, includes an inner conductive layer, an outer conductive layer, and a resistor layer between the conductive layers. The conductive layers and resistor layer are separated by insulating layer. In a further embodiment, a plated feedthrough is provided to connect to the resistor layer.

In a still further embodiment, the EMI shield is formed using a flexible circuit design. In this further embodiment, a specially designed illustrative plated through-hole is provided for connection to one or more of the conductive layers and resistor layer. Rather than having an ordinary pull-back region around the plated through-hole, the illustrative example does not pull back the outermost insulating layer at the plated through hole. Instead, an outermost insulating layer on one side of the EMI shield at the plated through hole is left undisturbed during flex circuit assembly. Once the flex circuit is assembled, a laser is used to pierce a hole in the outermost insulating layer at the specially designed through-hole. By this design, opportunities for arcing between plated through holes are minimized without unduly complicating the manufacturing process at the device level.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
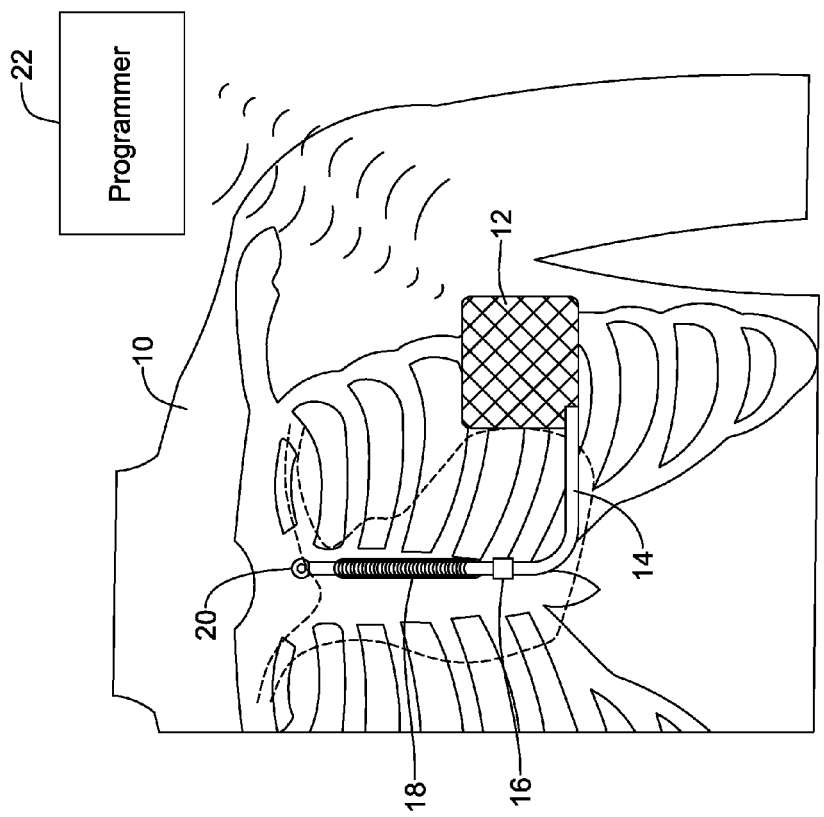
FIG. 1 shows an illustrative implantable medical device system implanted in a patient.

FIG. 1 shows an illustrative implantable medical device system implanted in a patient. This particular example show a subcutaneous cardiac device system implanted in a patient 10, over the patient's ribs and beneath the skin. A canister 12 is implanted, in the example, at approximately the left axilla (armpit), beneath the arm. A lead 14 extends from the canister 12 toward the patient's xiphoid and then over or slightly to the left of the sternum and toward the manubrium. The lead 14 includes electrodes 16, 18 and 20, with electrode 18 illustrated as a coil electrode designed primarily for shock delivery (though sensing via coil electrode 18 may be performed as well). The other electrodes 16 and 20 on lead 14 are shown as ring and cap electrodes, respectively. Other designs may be used. The canister 12, in this example, includes a conductive surface or, if desired, has an area on its surface which is conductive to allow for at least sensing of electrical signals and, when needed, therapy delivery.

A programmer 22 is provided for communicating with and controlling operation of the implanted system, as is well known in the art. Such communication can be useful to configure the implanted system for sensing, therapy or other feature, to load new software or firmware for the implanted system, and to retrieve information about system operation such as device status, therapy history, diagnostic information (device and/or patient related), or other suitable data.

The medical device system of FIG. 1 is merely one illustration. Other configurations and implant locations may be used instead. Cardiac devices may be implanted in other subcutaneous locations, transvenous systems, epicardial systems, intravascular systems and may include therapy delivery systems or monitoring devices. For example the canister 12 may be located elsewhere, and/or the lead 14 may enter the circulatory system, wrap around to the back of the patient, or pass beneath the ribs of the patient.

Other active implantable devices include drug or insulin pumps, proposed artificial pancreas devices, and neurostimulation or neuromodulation systems which can be used in numerous ways such as pain treatment, seizure prevention, treatment of progressive diseases such as Parkinson's or Alzheimer's disease, therapy for digestive or breathing disorders, and many others undergoing research and development. Some illustrative examples may be implemented in these other implantable devices.

The canister 12 may contain operational circuitry for controlling the operation of the device including, for example, various logic circuits, amplifiers, filters, and, often, a microcontroller or microprocessor. Communication circuitry may be provided for use in one or more of inductive, RF or conducted communication. This operational circuitry may be provided on a one or more "hybrids", usually a circuit board (often a flexible circuit or rigid-flex circuit) having the relevant application specific integrated circuitry, processors and logic. More than one hybrid may be used, for example, a high power hybrid and a low power hybrid may be included, with coupling therebetween, to avoid high power functions interfering with low power functions. These devices will include batteries and, for those with high power therapy outputs, high power capacitors, or other separate circuitry such as an actuator for controlling the output of therapeutic substances, for example. Often a separate header is provided for allowing hermetically sealed connection to one or more leads or electrodes.

The illustrative example of FIG. 1 shows a subcutaneous-only implantable defibrillator. This recently available generation of devices uses approximately twice the energy (60 to 80 Joules) of the prior generation transvenous implantable defibrillators (up to 40 Joules). With higher energy comes higher voltages, presenting new challenges within the canister 12, including potential for Corona discharge or arcing between components and the canister surfaces during delivery of high energy defibrillation shocks. In particular, since the conductive surfaces of the canister 12 are used for therapy delivery, the canister 12 itself may be at a high voltage differential relative to system ground—for example there may be a voltage drop of more than 1000 volts between the canister and system components may occur during therapy delivery. A 1000 volt drop across a few millimeters of air may be sufficient to cause arcing, which can damage system components and circuitry, or may cause a reboot of the control system.

These issues and development of certain solutions are described in U.S. Pat. No. 7,769,457, titled ELECTROMAGNETIC INTERFERENCE SHIELDING IN AN IMPLANTABLE MEDICAL DEVICE, the disclosure of which is incorporated herein by reference. The '457 patent teaches, in part, that high voltage drops across air gaps should be avoided to prevent corona discharge. To do so, the '457 patent teaches a shield having a dielectric sandwiched between a first conductor layer which is tied to the device ground and a second conductor layer which is electrically tied to the canister.

In addition to managing corona discharge, implantable devices present challenges with respect to dumping unwanted charge, particularly with respect to implantable defibrillators. In one example, a dump resistor can be provided in the vicinity of the high power charging circuitry of the device. However, using a normal discrete component as a dump resistor can require a large resistor to avoid undue heat generation, extending the time required for dumping charge from capacitive storage, or multiple resistors that may occupy up precious space in the device. One prior approach used, for example, in the Progeny® family of devices marketed by Boston Scientific Corporation, is to provide a dump resistor on a flex circuit, with the flex circuit placed adjacent to the battery and capacitor of the device such that the battery and capacitor act as heat sinks, allowing any heat generated during charge dump to be dispersed over a large area.

Figure 2:
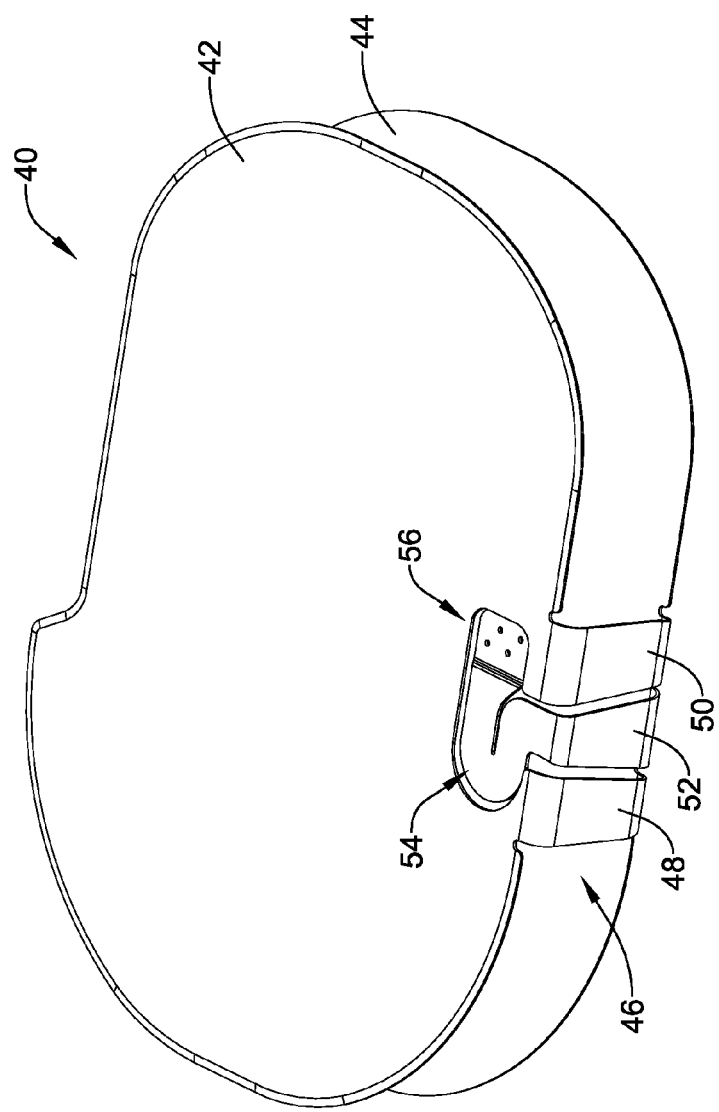
FIGS. 2-4 show details of an illustrative EMI shield for an implantable medical device.
Figure 3:
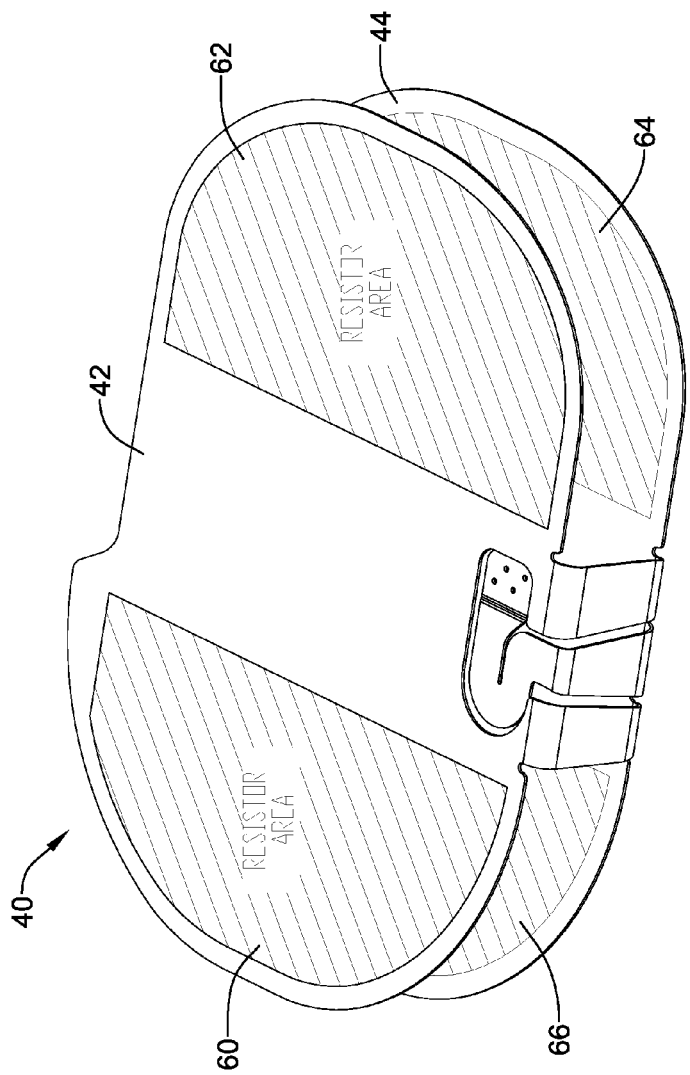
Figure 4:
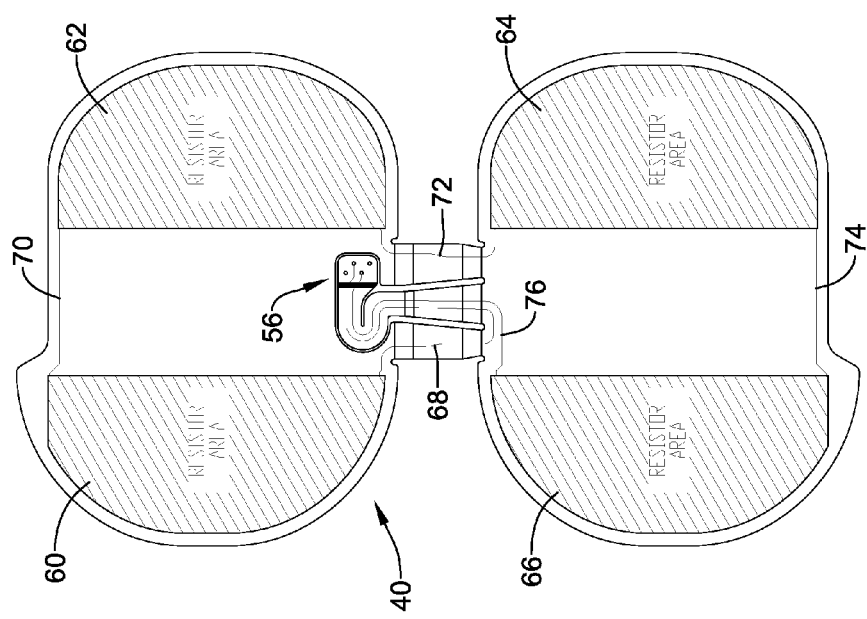

FIGS. 2-4 show details of an illustrative EMI shield for an implantable medical device. As shown in FIG. 2, the EMI shield 40 includes first leaf 42 and second leaf 44, connected together with a connection structure 46 including first and second arms 48, 50, and an electrical connector 52 which includes an optional strain relief 54 and coupling location 56. The strain relief 54 may be a strain relief as described in US Provisional Patent Application No. 62/143,388, titled IMPLANTABLE MEDICAL DEVICES WITH FLEXIBLE INTERCONNECT HAVING STRAIN RELIEF, the disclosure of which is incorporated herein by reference.

The illustrative shield 40 in FIG. 2 is shown in a wrapped configuration corresponding to how it would wrap around the components and operational circuitry of an implantable medical device. Further details are shown in FIG. 3, which illustrates the placement of flexible resistors in the shield 40. As shown, shield leaf 42 includes resistor areas 60 and 62, and shield leaf 44 includes resistor areas 64 and 66. As further shown in FIG. 4, the shield 40 includes a number of traces connecting together the resistor areas. Thus, trace 68 connects a pin of the coupling location 56 to resistor area 60, trace 70 connects resistor area 60 to resistor area 62, trace 72 connects resistor area 62 to resistor area 64, and trace 74 connects resistor area 64 to resistor area 66. Trace 76 links the resistor circuit 60-70-62-72-64-74-66 back to the electrical connector 56.

Each resistor area 60, 62, 64, 66 comprises a pattern of a resistive material such as a Copper-Nickel alloy, and the traces place the four resistor areas 60, 62, 64, 66 in series. In an illustrative example, the individual resistor areas include a long, winding trace of Copper-Nickel alloy (CuNi 715), made by removing a pattern from a foil layer. Other patterns and materials may be used; including, for example, the Iconel alloys having predominantly Nickel with Chromium as a second element, such as Iconel 625. In one working example, the resistive material lines are 6 mils (0.006 inches) wide, spaced by 6 mils, with a thickness of 0.000625 inches, with a total length of the resistive trace of about 585 inches, to yield a resistance of about 2.5 kilohms. Other dimensions, patterns and materials may be used to provide desired areas, spacing and overall resistance.

As used herein, a "resistive" or "resistor" layer is a layer in which the dimensions and material properties of an otherwise conductive material are manipulated to provide a resistor of a predictable range of values. Generally, a layer can be deemed a resistor layer by virtue of having a planned resistance in the range of more than about 10 ohms and a design allowing current to be passed therethrough between first and second access points.

Because implantable medical devices are of particular interest in several embodiments, heating is generally to be minimized. Since higher currents cause more heat, in several embodiments a resistor layer may have an impedance of more than 500 ohms, and preferably in the range of about 1 to 10 kilohms. High power/voltage outputs of implantable medical devices often are delivered from capacitors or capacitor banks. Therefore, it may be preferable to keep the dump resistor value in a reasonably low range below, for example, below 50 kilohms, to avoid large RC time constants and long dump times. However, unless explicitly stated in the claims, these ranges should be viewed as merely illustrative and explanatory; larger and smaller resistances may be used.

Figure 5:
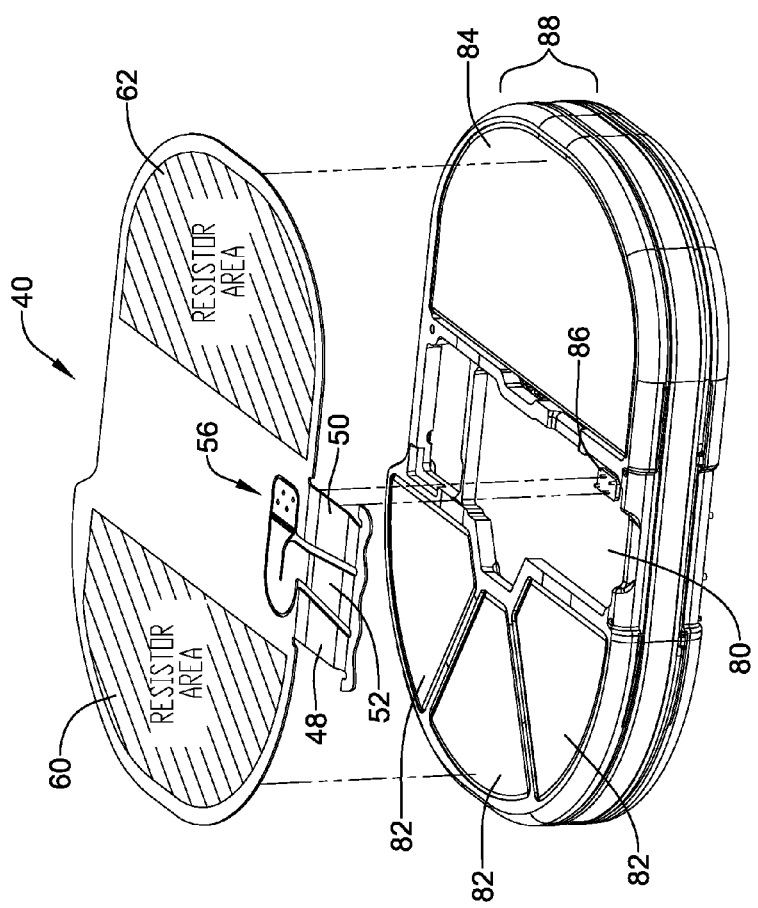
FIG. 5 shows how an illustrative EMI shield may be placed relative to various components of an implantable medical device.

FIG. 5 shows how an illustrative EMI shield may be placed relative to various components of an implantable medical device. One leaf of the shield 40 is shown in relation to the operational circuitry 80, capacitor stack 84 and batteries 82 of the implantable device. As can be observed, the resistor area 60 is sized and shaped to generally match the area taken up by the batteries 82, while resistor area 62 is sized and shaped to generally match the area taken up by the capacitor stack 84. The resistor layer does not include a pattern in the area that overlies the operational circuitry 80. While it is not necessary to leave this region blank, for heat sink purposes the intimate contact of the shield 40 with the batteries 82 and capacitors 84 is useful, as each of these will generally contain a number of anode/cathode plates immersed in a solution.

If a larger resistance is desired, some designs may omit the gap between resistors 60 and resistor 62. In one example, different areas of the shield 40 may have different patterns of traces to manipulate where heat can be generated. For example, a resistor area could cover the entire face of the shield 40, which some areas having lower density of resistive elements, or thicker traces, than other areas, to reduce power dissipation in regions having less heat sink availability.

The arms 48, 50 are designed to wrap around the thickness 88 of the components 82/84 and operational circuitry 80 to another leaf (not shown) of the shield 40. In addition, it can be seen that the electrical connector 52 is sized and shaped to position the coupler 56 adjacent pins 86 of the operational circuitry 80. The pins 86 may be positioned, for example, on a high-power hybrid circuit, or other portions of the operational circuitry 80, as desired.

Figure 6:
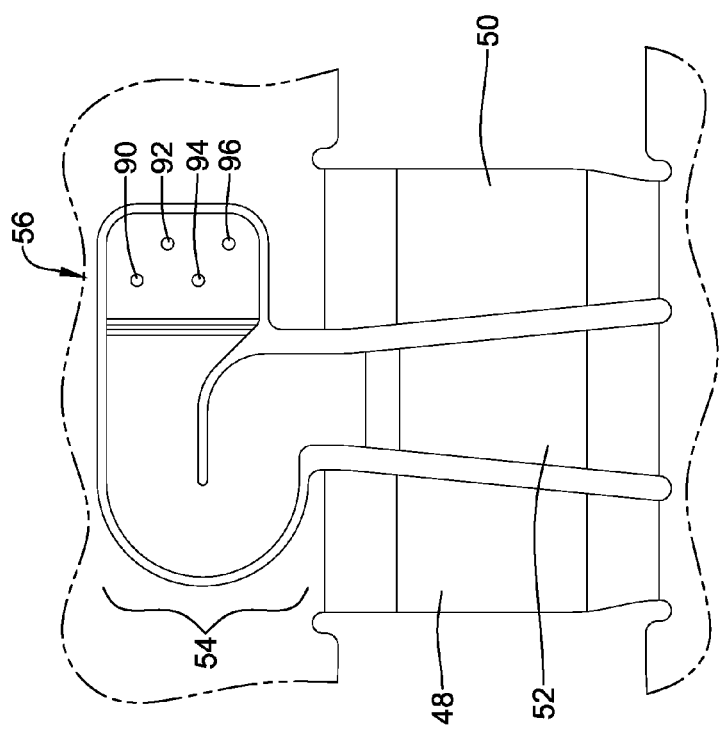
FIG. 6 highlights certain details of a connector for an EMI shield.

FIG. 6 highlights certain details of a connector for an EMI shield. The arms 48, 50 run along either side of the electrical connector 52, which is separated by a strain relief structure 54 from the electrical coupling location 56. Further details of the strain relief structure 54 are discussed in U.S. Provisional Patent Application No. 62/143,388, titled IMPLANTABLE MEDICAL DEVICES WITH FLEXIBLE INTERCONNECT HAVING STRAIN RELIEF, the disclosure of which is incorporated herein by reference. The coupling location 56 includes four through-holes 90, 92, 94, 96 in this example. The through holes 90, 92, 94, 96 may be of conventional design or, preferably, are manufactured by methods further explained below in association with FIGS. 13-14, to reduce the opportunity for electrical arcing.

Figure 7:
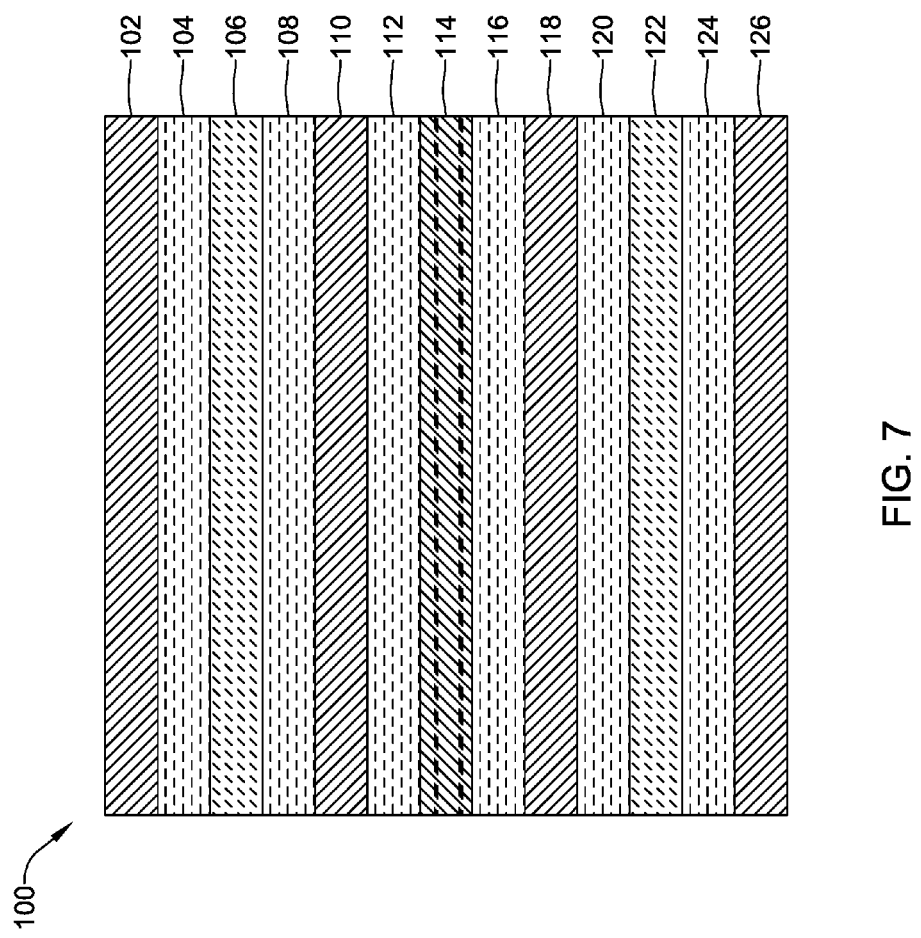
FIG. 7 shows a cross section of an illustrative EMI shield.

FIG. 7 shows a cross section of an illustrative EMI shield 100. An insulating cover layer 102 is coupled by adhesive 104 to a first conductor layer 106. The first conductor layer 106 is coupled by adhesive 108 to a second insulation layer 110. The second insulation layer is coupled by adhesive 112 to a resistor layer 114, which couples to a third insulation layer 118 by adhesive 116. Another adhesive layer 120 couples the third insulation layer 118 to a second conductive layer 122, which is attached to a second cover layer 126 by still another layer of adhesive 124.

Not all of the layers shown are needed in any given embodiment, and one or more may not appear at all locations within a given shield. For example, in one working embodiment, the adhesive layers 108 and 120 are omitted. This makes for a thinner shield and greater flexibility. In another example, the conductive layers 106, 122, and the resistor layer 114, are patterned as shown further below. With the conductive layers 106, 122 patterned, then there are locations where adhesive layer 104 is adhered to each of the insulation layers 102 and 110, preventing delamination of the overall structure even if there is no adhesive 108 securing the insulation layer 110 to the conductor layer 106.

In addition, the illustration of FIG. 7 is not drawn to scale, as some layers are thinner than others. In a working example that omits layers 108 and 120, the thicknesses are as follows:

| Material | Layer | Working Thickness |
|---|---|---|
| Insulation | 102 | 17.5 μm |
| Adhesive | 104 | 25 μm |
| Conductor | 106 | 18 μm |
| Insulation | 110 | 25 μm |
| Adhesive | 112 | 25 μm |
| Resistor | 114 | 16 μm |
| Adhesive | 116 | 25 μm |
| Insulation | 118 | 25 μm |
| Conductor | 122 | 18 μm |
| Adhesive | 124 | 25 μm |
| Insulation | 126 | 17.5 μm |
| Total Shield Thickness | | 237 μm |

Further embodiments may use layers which are thicker or thinner, for example, thicknesses may be as much as doubled that shown, or one-third of that shown in the working example. Some examples will use additional layers.

In an illustrative example, the insulating layer is a polyimide layer, though any suitable insulator may be used. Common insulating materials include polyimide, fluorinated ethylene propylene (FEP), and polyester films, though other materials may also be used. The multi-layer structure can be secured together using an adhesive such as an acrylic or epoxy.

In an illustrative example, the conductive layers may be made of any suitable material. Common conductor materials include copper, nickel, gold, silver, tin, alloys of copper (such as phosphor bronze and beryllium copper), ferrous alloys, and nickel alloys (such as copper-nickel and nickel-chromium), as well as various other materials such as stainless steel. For medical devices, non-ferrous materials are often preferred.

Different materials may be used in different layers, if desired. The resistor layer in an example is a copper-nickel alloy, but may also be any suitable material including for example tin, nickel, stainless steel or nickel-chromium alloys. In some examples a single material may be used for all three layers, with the only difference being that a specific pattern is used for the resistor layer to create a long, thin resistor.

Still further embodiments may use thicknesses dictated by electrical requirements, for example, for a given insulating dielectric, conductor(s), and adhesive layers, the thicknesses may be determined by system voltage requirements, to ensure adequate dielectric protection between layers. The thickness, width and length of the resistor layer traces may be determined by a combination of the desired resistor value, the material properties used for the resistor, and the quantity of current to be sunk. Distance between resistor traces may be controlled to ensure adequate dielectric protection as well, as the voltage drop from one line to the next should be understood so as to avoid dielectric breakdown. Thicknesses may be controlled as well to take into consideration the resultant capacitance. Other characteristics may also be considered as fits the needs of a particular application.

In one embodiment, referring to FIG. 2, the connection area 46 between leafs 42, 44 may omit one of the conductor layers (and its adjacent cover layer and adhesive) to obtain a thinner and more flexible connection area 46. For example, referring to FIG. 7, layers 120, 122, 124 and 126 may be omitted in the connection area 46. In another example, the second connector layer 122 (along with layers 120, 124 and 126) is omitted in only the electrical connector 52 (FIG. 2) but is included in the connector arms 48, 50 (FIG. 2).

By placing the dump resistor in the EMI shield, the opportunity to have arcing between components or the device housing and the dump resistor is also avoided. During a dump process, the resistor is positioned such that the dielectric between it and the inner and outer shield layers will absorb any high voltage fields.

Figure 8:
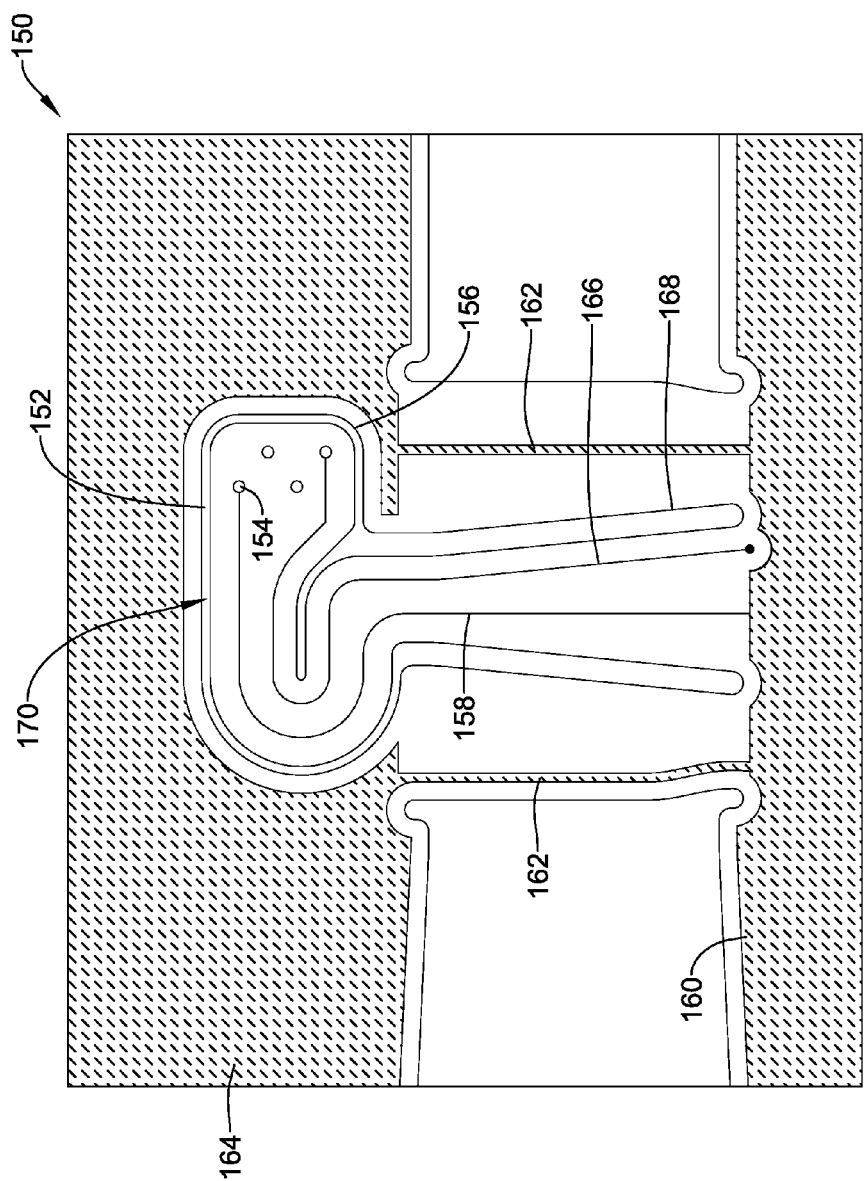
FIGS. 8-10 show layer-by-layer details of an illustrative EMI shield.
Figure 9:
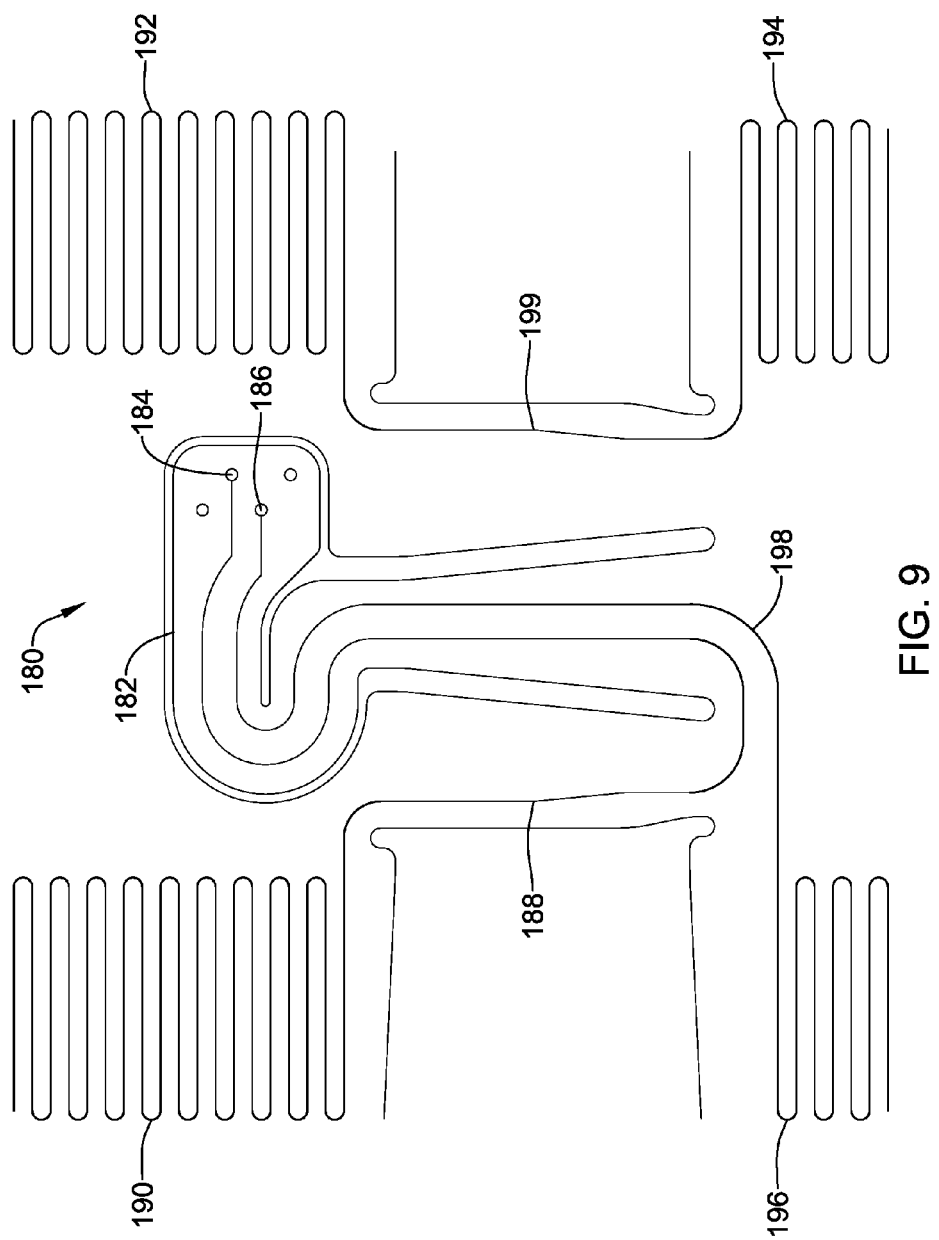
Figure 10:
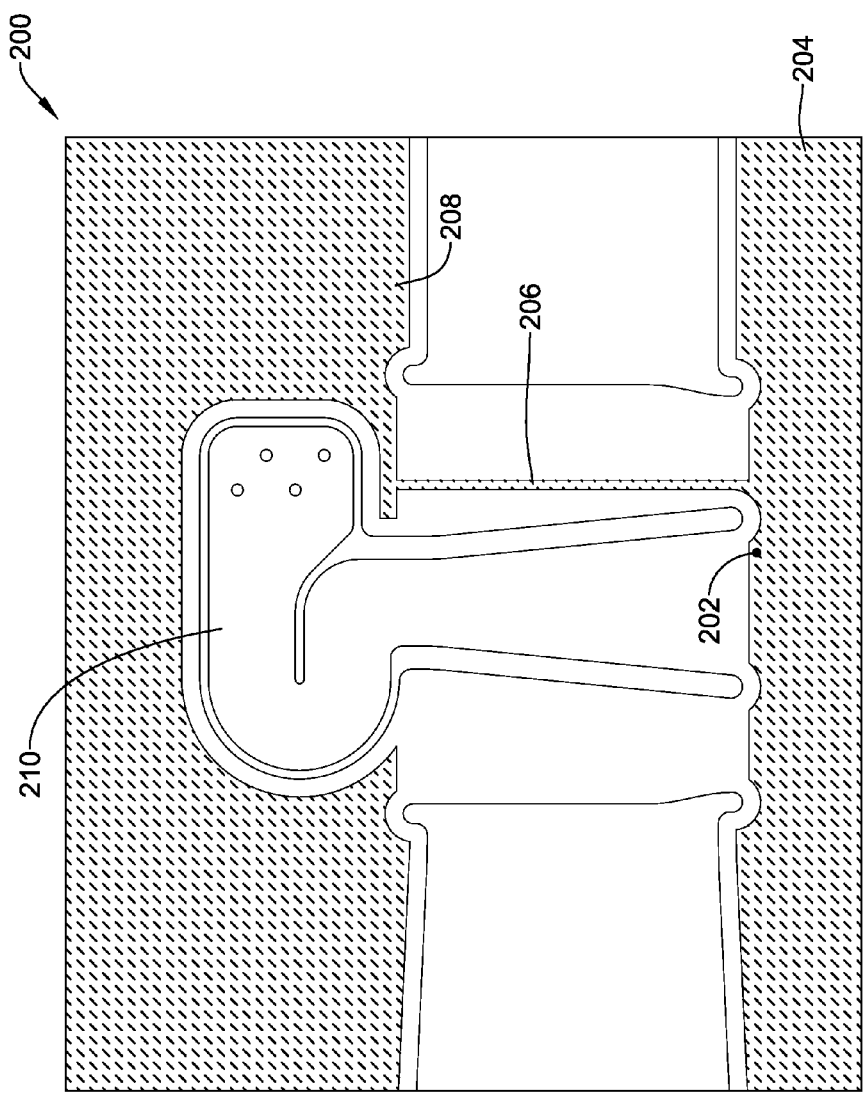

FIGS. 8-10 show layer-by-layer details of an illustrative EMI shield. FIG. 8 shows a first one of the conductive layers 150. The connection area 152 is illustrated with through holes which include through holes 154 and 156. One through hole 154 is connected by a trace 158 to a first conductive region 160. Two traces 162 link the first conductive region 160 to a second conductive region 164 on the other leaf of the EMI shield. Through-hole 156 is connected to a trace 166 which leads to through-hole 168 for connection to the second conductive layer, shown below in FIG. 10. Through-hole 156, trace 166, and through-hole 168 are provided on the first conductive layer in order to allow the second conductive layer (FIG. 10), and associated adhesive and insulator layers, to be omitted throughout the electrical connector 170, enhancing the flexibility of the electrical connector 170.

FIG. 9 shows the resistor layer 180. The connector 182 is illustrated with two of the through-holes 184, 186 being associated with traces 188, 198 on the resistor layer. Trace 188 leads to a first resistor area 190, which is connected to a second resistor area 192 by another trace (not shown) located near an outer edge of the illustrative EMI shield. As illustrated at 199, another trace connects second resistor area 192 to a third resistor area 194. Again, a trace (not shown) located near the outer edge of the illustrative EMI shield links together the third resistor area 194 and fourth resistor area 196. Trace 198 connects the fourth resistor area 196 back to the through hole 186 for electrical coupling to the electronics of an implantable medical device, The four resistor areas 190, 192, 194, 196 are shown having a pattern of a single continuous line which winds back and forth across the resistor layer. This provides a very long trace. In one example, a layer of foil of 6 mils of resistive material (copper-nickel alloy (CuNi-715)) is patterned to 6 mils in width, with spacing between lines of 6 mils, providing a total length of about 585 inches of resistive material and a total resistance of approximately 2.5 kilohms. For illustrative purposes the line 190/192/194/196 is shown well out of proportion. Other patterns, dimensions, and materials may be used.

In this illustrative example, the four resistor areas 190, 192, 194, 196 are generally sized and shaped similar to that shown in FIGS. 3-5, above. In particular, because energy will be dissipated in the four resistor areas 190, 192, 194, 196 during a charge dump, the four resistor areas 190, 192, 194 and 196 may correspond to the high voltage capacitors and the batteries of an implantable medical device, each of which can serve as a heat sink for dissipated energy. This approach avoids the generation of excess heat and/or creation of observable hot spots during a charge dump.

FIG. 10 illustrates the second conductive layer 200. This second conductive layer 200 includes a connection to a through-hole 202, which is connected to the conductive layer at 204. A trace 206 connects conductive layer 204 to conductive layer 208. As noted above, in this particular example, the second conductive layer is entirely omitted from the connection area 210, making this region of the EMI shield more flexible than the rest.

Figure 11:
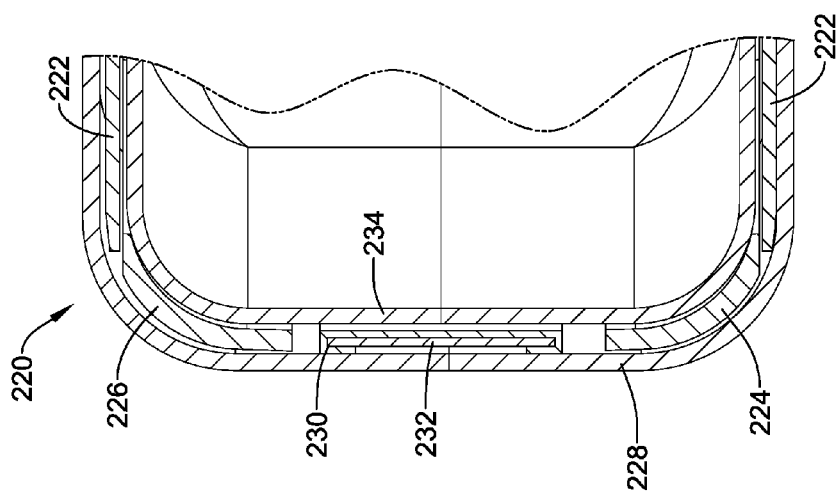
FIG. 11 illustrates the disposition of an illustrative EMI shield at the edges of an illustrative device canister.

FIG. 11 illustrates the disposition of an illustrative EMI shield at the edges of an illustrative device canister. A corner of a device 220 is illustrated in partial cross-section, with the shield 222 adjacent to liner sections 224 (lower) and 226 (upper) to separate the outer housing 228 of the device 220 from the battery or capacitor canister 234. A weld ring insulator 230 wraps around a weld ring 232, which is used in welding the two halves of the housing 228 together during manufacturing to shield the internal electronics and to provide a surface against which welding may occur.

Some or all of the housing 228 may be conductive using a variety of materials known in the art. Likewise, the battery or capacitor canister 234 is typically a conductive metal, often provided with an outer protective coat of non-conductive material, for example, paraffin, for sealing, handling and/or manufacturing purposes. In some embodiments, the shield 222 may extend further around the edges of the battery or capacitor canister 234 to the weld ring, if desired. In one example, the liner sections 224, 226 may be connected together and may include a dielectric and one or more metal layers. The weld ring insulator 230 may also include a simple dielectric or may have multiple layers.

FIG. 11 provides an opportunity to explain the EMI shield performs its function relative to electrical fields. The outer conductive layer, shown in FIG. 8, above, may be electrically linked—for example, shorted—to the conductive housing 228 of the device during delivery of a high voltage therapy, such as a defibrillation shock. This electrical linkage eliminates the possibility of corona discharge or arcing across air gaps between the EMI shield and the housing of the device, as there is no voltage drop across the air gaps that can lead to arcing. Without the EMI shield in place, such arcing could occur between the housing and components and circuitry within the implantable device, as described in commonly assigned U.S. Pat. No. 7,769,457, titled ELECTROMAGNETIC INTERFERENCE SHIELDING IN AN IMPLANTABLE MEDICAL DEVICE.

The inner conductive layer shown in FIG. 10, above, may be electrically linked—for example, shorted—to the ground plane or other reference voltage or VBat, the battery circuit output voltage, of the implantable system. As a result, if the conductive housing of the device is at a high voltage during shock delivery, the voltage drop from high voltage to a reference or ground voltage of the operational circuitry of the device takes place within the dielectric layers of the EMI shield.

During a high voltage shock delivery, the resistive layer between the inner and outer conductive layers may be isolated from the remainder of the circuit and left to float, if desired. Alternatively, the resistive layer between the inner and outer conductive layers may be tied to a different reference voltage, an intermediate voltage, to ground, or to the high voltage output.

Defibrillation therapy is often delivered in a biphasic waveform. Therefore it should be noted that references to "high voltage" herein are intended to encompass high magnitude voltages, and include both positive and negative voltages with magnitudes over 250 volts.

Figure 12:
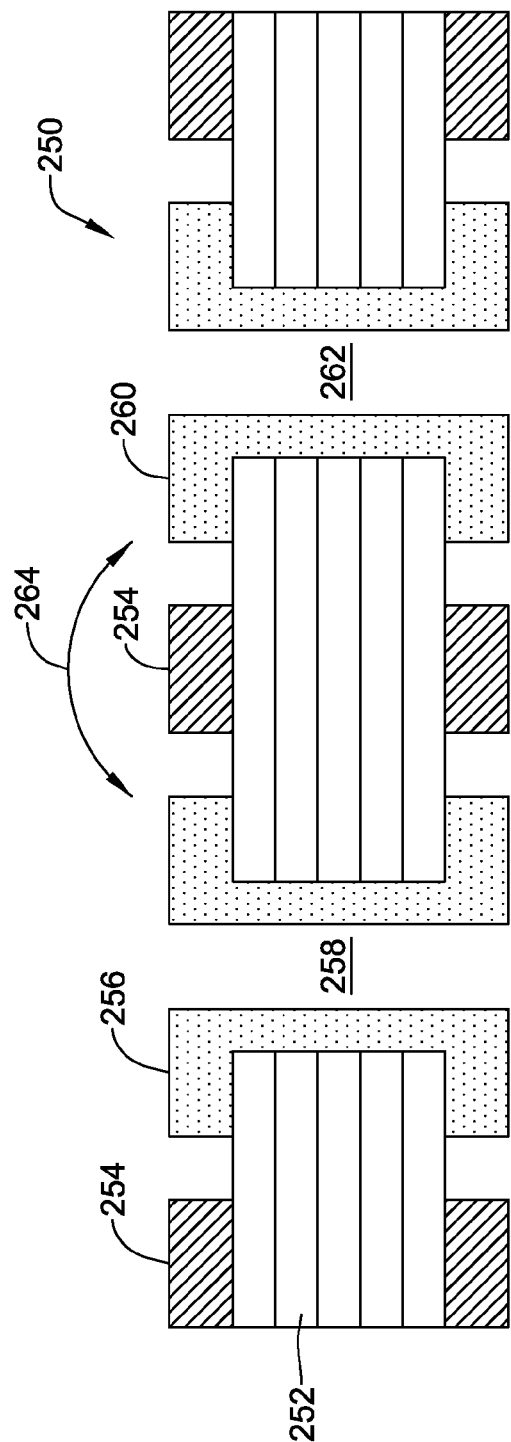
FIG. 12 shows a prior art plated through-hole.

FIG. 12 shows a prior art plated through-hole. An illustrative portion of a flex circuit is shown at 250 and includes a plurality of layers 252, with a cover layer 254 of dielectric. The conductive plating 256 of a through-hole 258 is shown, as well as conductive plating 260 of a second, nearby through-hole 262. In the prior art design, the cover layer 254 is pulled back (by removal or other known technique) from the through-holes 258, 262. For holes 258, 262 that are near one another, this leaves a small area of dielectric insulation 254 between the plating 256, 260. If the distance between through-holes is small, and the voltages in use are high, the design creates an opportunity for arcing at 264 between the plating 256. Spacing the through-holes at wider distance from one another is one solution, but that can increase the space needed on the circuit boards and within the device.

Figure 13:
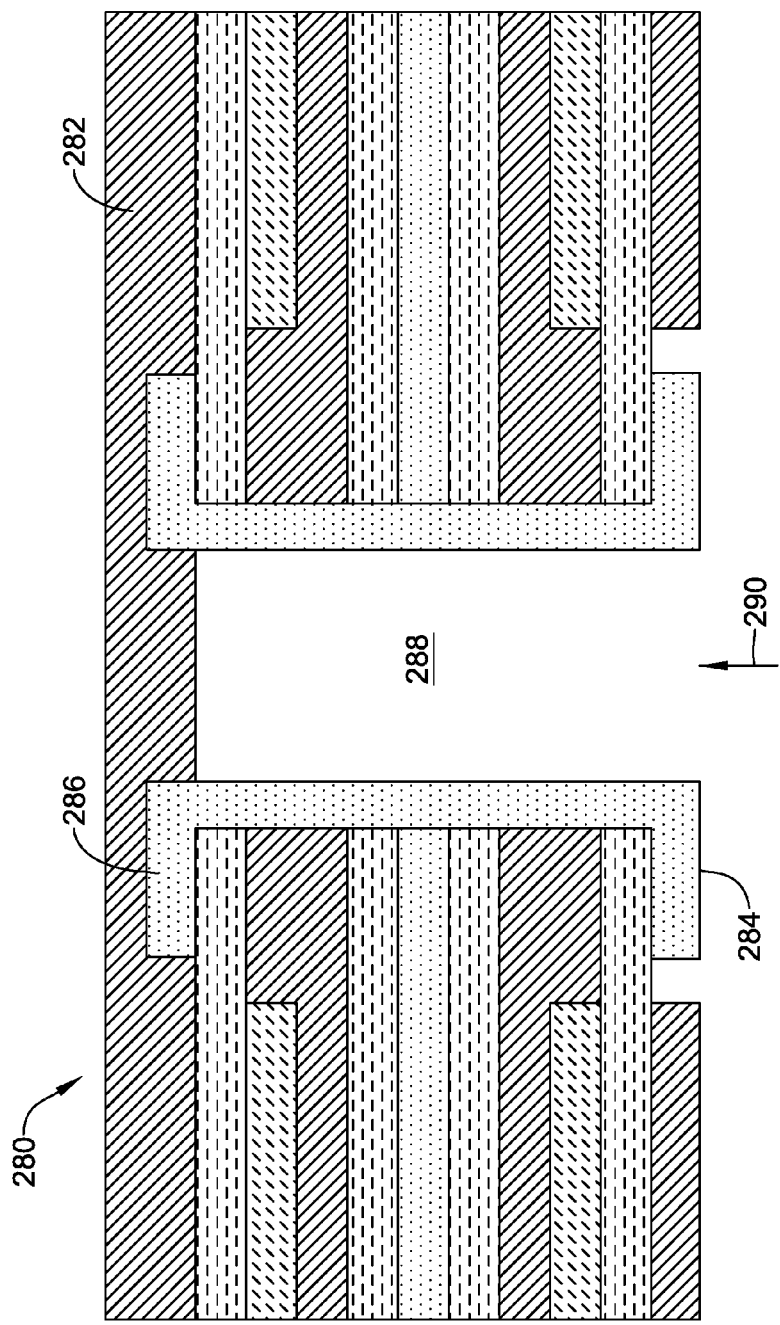
FIG. 13 highlights details of an unfinished, plated, through-hole for an illustrative embodiment.

FIG. 13 highlights details for a plated through-hole for an illustrative embodiment designed to prevent arcing between the plating of two closely placed through-holes. The example is shown at 280 and includes an insulative cover layer shown at 282. The through-hole plating is shown with header 284 on one side and header 286 on the other side around through-hole 288. Rather than including a pull-back region in the cover layer 282, in this example the cover layer 282 entirely covers the header 286.

To finish the manufacturing of the example in FIG. 13, a laser is used to remove the portion of the insulator layer over the through hole 288, but not over the header 286. To do so, a laser is applied in direction 290, going through the through-hole, rather than coming from the other direction. By applying the laser from direction 290, a limited portion of the insulator layer 282 is removed.

Figure 14:
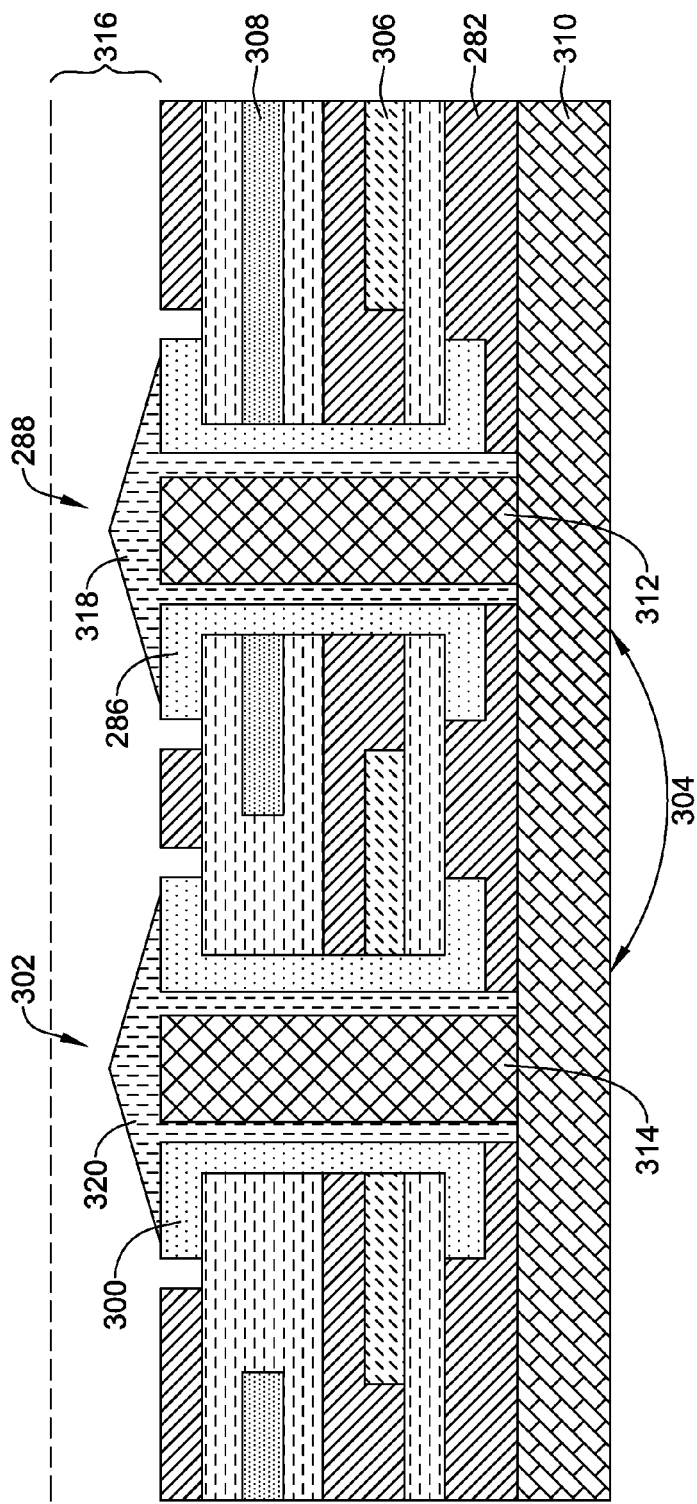
FIG. 14 shows finished through-holes of another illustrative embodiment.

FIG. 14 shows the finished product attached to a circuit board. As can be seen, only the portion of the cover layer 282 that covers the through-hole 288, as well as through-hole 302, has been lasered away. This leaves the insulating cover layer 282 over both header 286 and header 300, and minimizes the opportunity for arcing along line 304.

Some further details of the example in FIG. 14 are worth noting. The through hole 302 is connected to the outer conductive layer 306. An inner conductive layer is not shown since, in this example, the inner conductive layer and an associated insulation layer are omitted in the region of the electrical connectors. The plating at through-hole 288 is coupled to the resistive layer 308, rather than the conductive layer 306.

In use, the flex circuit 280 is secured to a substrate 310, which may also be a flex circuit, such as one of the hybrid circuits (the high-power hybrid, for example) of the implantable medical device. Pins 312 and 314 can be soldered 318, 320 to the plated through holes 288, 302, respectively. Also shown in FIG. 14 is an optional "glob" material layer 316, which may be, for example, a dielectric that can be flowed (while heated, with later cooling and solidification, or flowed at room/manufacturing temperature and subsequently cured, for example) over the solder 318, 320 to ensure no arcing occurs and to insulate the solder caps 318, 320 from other conductive components or foreign material. In some embodiments, the glob layer 316 can be omitted, or may be more limited to only cover the solder caps 318, 320.

Several examples are shown above as used in implantable medical devices. However, some concepts may also be implemented outside of the medical device context, for example, a plated through-hole design as shown in FIGS. 13-14 may be used in other applications of flexible circuitry having through-holes. A resistive layer design as shown in FIGS. 7-10 may be used in non-medical device applications that require shielding and current dumping capability, for example.

A first non-limiting example takes the form of an implantable medical device comprising a battery, operational circuitry coupled to the battery including at least a ground reference and an electrical therapy circuit, conductive housing containing both the battery and the operational circuitry, and a flexible shield separating the battery and operational circuitry from the conductive housing, the shield comprising a first conductive layer, a resistor layer, and a second conductive layer, the resistor layer being disposed between the first and second conductive layers. Referring to FIG. 5, such a device is shown with battery 82 and operational circuitry 80, which may include a charging circuitry for high voltage therapy using capacitor(s) 84 or other components or sub-circuits and may also include, for example, output circuitry (such as an H-bridge circuit) for outputting therapy circuitry, with a flexible shield 40 disposed thereabout to separate the battery and operational circuitry from a housing (not shown in FIG. 5, but seen in FIG. 1 at 12. The inclusion in the shield 40 of the first conductive layer 106, resistor layer 114, and second conductive layer 122 can be seen in FIG. 7. A ground reference in the operational circuitry may be coupled for example to the negative voltage terminal of the battery 82, or to some other setpoint using common circuit components.

A second non-limiting example takes the form of a further embodiment of the first non-limiting example includes wherein the flexible shield is connected to the operational circuitry such that the operational circuitry comprises a plurality of switches configured to: selectively place the first conductive layer electrically in common with the conductive housing; selectively place the second conductive layer electrically in common with the ground reference; and selectively couple the resistor layer to the electrical therapy circuit as a dump resistor for selectively dumping electrical charge. In FIG. 5, the operational circuitry 80 includes connection pins at 86 for coupling with the electrical connector 52 of the shield 40, and the inclusion of switches for performing such coupling to the various layers of the shield can include, for example, various semiconductor circuits including silicon-controlled rectifiers, field effect transistors, junction transistors and the like. Selective dumping of electrical charge may take place for example if therapy preparations are begun, but therapy is not delivered (if for example a deadly arrhythmia reverts to normal rhythm before therapy is delivered). Dumping may also be performed following periodic capacitor reformation, which is done every so often (typically one to three times a year) to ensure adequate performance of the capacitors of the implantable device. As an alternative to this second non-limiting example, the first conductive layer may be permanently connected, electrically, to the conductive housing, and the second conductive layer may be permanently connected, electrically, to the ground reference of the device. It may be noted in either the second non-limiting example and/or its alternative that the shield may be disposed within the conductive housing so that the first conductive layer is closer to the housing than the second conductive layer and the second conductive layer is closer to the operational circuitry, battery and capacitor than the first conducive layer. For this configuration, in an assembled device, the first conductive layer is the "outer" conductive layer of the shield, and the second conductive layer is the "inner" conductive layer of the shield.

In a third non-limiting example, a furtherance of the second non-limiting example includes the operational circuitry being configured to deliver a high power therapy shock by, at least in part: placing the first conductive layer electrically in common with the conductive housing by closing a switch; and placing the second conductive layer electrically in common with the ground reference by closing a switch. Such a process is described with reference to the illustration in FIG. 11, above.

A fourth non-limiting example may take the form of any of the first to third non-limiting examples, wherein the flexible shield comprises a plurality of insulating layers formed of materials selected from the group consisting of polyimide, fluorinated ethylene propylene (FEP), and polyester, or blends thereof. A fifth non-limiting example may take the form of any of the first to fourth non-limiting examples, wherein the plurality of insulating layers comprises a first insulating layer disposed between the first conductive layer and the resistor layer, a second insulating layer disposed between the resistor layer and the second conductive layer, and a third insulating layer covering the second conductive layer, such that the first conductive layer is exposed for contact with the conductive housing. A sixth non-limiting example may take the form of any of the first to fourth non-limiting examples wherein the plurality of insulating layers comprises a first insulating layer covering the first conductive layer, a second insulating layer between the first conductive layer and the resistor layer, a third insulating layer between the resistor layer and the second conductive layer, and a fourth insulating layer covering the second conductive layer. A seventh non-limiting example may take the form of any of the first to sixth non-limiting examples wherein the conductive layers comprise copper and the resistor layer comprises an alloy of copper and nickel.

An eighth non-limiting example may take the form of any of the first to seventh non-limiting examples further comprising a high power capacitor for use by the electrical therapy circuit, the high power capacitor being separated from the conductive canister by the shield. A ninth non-limiting example may take the form of the eighth non-limiting example wherein the resistor layer includes patterned regions and blank regions, wherein the patterned regions are shaped and sized such that, when the shield is placed to separate the battery, high power capacitor and operational circuitry from the conductive housing, the patterned regions substantially correspond to the locations of the battery and capacitors, and the blank regions correspond to the operational circuitry.

A tenth non-limiting example may take the form of any of the first to seventh non-limiting examples wherein the resistor layer includes patterned regions and blank regions, wherein the patterned regions are shaped and sized such that, when the shield is placed to separate the battery and operational circuitry from the conductive housing, the patterned regions substantially correspond to the location of the battery. An eleventh non-limiting example may take the form of any of the first to tenth non-limiting examples wherein the patterned regions of the resistor layer comprise an elongated trace of resistive material patterned to curve back and forth across the patterned region to define a resistor having a length and a width.

A twelfth non-limiting example may take the form of any of the first to eleventh non-limiting examples further comprising a plated through-hole coupled to the resistor layer between the first conductive layer and the second conductive layer. A thirteenth non-limiting example may take the form of the twelfth non-limiting example, wherein the plated through-hole coupled to the resistor layer includes a first side and a second side, the first side being closer to the first conductive layer and the second side for placement adjacent the operational circuitry, wherein a first insulating layer covers the first conductive layer and the plated through hole includes a first header on the first side and a second header on the second side, wherein the first conductive layer substantially covers the first header. A fourteenth non-limiting example may take the form of the thirteenth non-limiting example, wherein the plated through-hole is adjacent an opening in the first insulating layer, the opening formed by laser removal of a portion of the first insulating layer, wherein the laser removal is performed to avoid exposing the header through the first insulating layer.

A fifteenth non-limiting example may take the form of any of the first to eleventh non-limiting examples further comprising a plated through-hole coupled to at least one of the first conductive layer, second conductive layer or the resistor layer, the plated through-hole including a first side and a second side, the first side being closer to the first conductive layer and the second side for placement adjacent the operational circuitry, wherein a first insulating layer covers the first conductive layer and the plated through hole includes a first header on the first side and a second header on the second side, wherein the first conductive layer substantially covers the first header. A sixteenth non-limiting example takes the form of the fifteenth non-limiting example, wherein the plated through-hole is adjacent an opening in the first insulating layer, the opening formed by laser removal of a portion of the first insulating layer, wherein the laser removal is performed to avoid exposing the header through the first insulating layer.

A seventeenth non-limiting example takes the form of a method of manufacturing an electromagnetic shield for an implantable medical device comprising: manufacturing a flex circuit comprising at least a first insulation layer, a first non-insulation layer, and a second insulation layer, with the first non-insulating layer disposed between the first and second insulation layers, the flex circuit including a first plated through hole for electrical connection to the first non-insulating layer, the first plated through hole including a first header for disposition on the same side of the non-insulating layer as the first insulation layer, and a second header for disposition on the same side of the non-insulating layer as the second insulation layer, the first and second headers and the first plated through hole defining a lumen therethrough, wherein the flex circuit is manufactured such that the first insulation layer includes a portion that covers the first header to close one end of the lumen through the first plated through hole; applying laser energy through the first plated through-hole lumen to the first insulation layer to substantially remove the portion of the first insulation layer which covers the lumen, while leaving substantially undisturbed a portion of the first insulation layer covering the first header; wherein the first non-insulation layer is either a conductor layer having substantially conductive properties for providing equipotential connections, or a resistive layer having resistive properties for providing voltage dissipation between two connection points. Such a method of manufacturing including the plated through hole design and process is illustrated in FIGS. 13-14 and accompanying text.

An eighteenth non-limiting example takes the form of a method as described in the seventeenth non-limiting example, wherein the step of manufacturing the flex circuit includes placing at least a second plated through hole having first and second headers and a lumen therethrough for which the first insulating layer again covers the first header and closes one end of the lumen, wherein the step of applying laser energy also includes substantially removing a portion of the first insulation layer which covers the lumen of the first header of the second plated through hole, while leaving substantially undisturbed a portion of the first insulation layer that covers the first header of the second plated through hole. FIG. 14 illustrates such a design. A nineteenth non-limiting example takes the form of either of the seventeenth or eighteenth non-limiting examples, wherein the steps of manufacturing the flex circuit and applying the laser energy are performed to substantially prevent shorting or arcing between the first header of the first plated through hole and the first header of the second plated through hole.

A twentieth non-limiting example takes the form of a method of manufacturing an implantable medical device (IMD) comprising a battery, capacitors and operational circuitry for the IMD configured for electrical connection with one another, wherein the operational circuitry includes a dump circuit, a ground reference and at least a first high voltage output line, the method comprising wrapping a flexible shield around the battery, capacitors and operational circuitry, the flexible shield comprising first and second conductive layers around a resistor layer with a plurality of insulation layers; electrically coupling the flexible shield to the operational circuitry either before or after the wrapping step, such that the first high voltage output line is coupled to the first conductive layer, the ground reference is coupled to the second conductive layer, and the dump circuit is coupled to the resistor layer, placing the flexible shield into a conductive housing for the IMD before, between, or after the wrapping and electrically coupling steps; electrically coupling the conductive housing to the first high voltage output line; and hermetically sealing the conductive housing of the IMD. Such a method is shown across the several figures. As shown in FIG. 5, the battery 82, capacitor 84 and operational circuitry 80 are placed in a relatively compact configuration and, at the stage shown in FIG. 5, would be already electrically coupled one to another including, for example, coupling the battery 82 to power the operational circuitry 80, and coupling the capacitor 84 to the high voltage charging circuitry of the operational circuitry 80 to enable charge storage during preparation for high voltage therapy delivery. As described and illustrated above, using for example the combination of FIGS. 4-5, the shield 40 is wrapped about the circuitry 80 with battery 82 and capacitor 84, and the electrical connector 52 is coupled to the operational circuitry by soldering or otherwise securing element 56 to element 86. These elements are then placed into a canister such as electrically conductive canister 12 shown in FIG. 1, and as noted above the high power outputs of the operational circuitry 80 (FIG. 5) and capacitor 84 (FIG. 5) are coupled to the canister and lead 14 (FIG. 1) for therapy delivery, while also coupling to the shield layers in the shield 40 and the dump resistor in the shield 40 in the case a charge dump is needed. Hermetic sealing is performed to achieve the structure in FIG. 11, with the shield 222 between and wrapped around the circuitry (here, the battery or capacitor 234 is shown), and a weld shield 232 within a weld shield insulator 230 used to protect the inner workings of the device during welding of the canister 228 along the line adjacent the weld shield 232. As is known to those skilled in the art, the hermetic sealing can include the addition of a header for coupling to a lead, for example, as shown in FIG. 1.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
    a battery;
    operational circuitry coupled to the battery including at least a ground reference and an electrical therapy circuit;
    a conductive housing containing both the battery and the operational circuitry; and
    a flexible shield separating the battery and operational circuitry from the conductive housing, the shield comprising a first conductive layer, a resistor layer, and a second conductive layer, the resistor layer being disposed between the first and second conductive layers.

2. The implantable medical device of claim 1 wherein the flexible shield is connected to the operational circuitry such that the operational circuitry comprises a plurality of switches configured to:
    selectively place the first conductive layer electrically in common with the conductive housing;
    selectively place the second conductive layer electrically in common with the ground reference; and
    selectively couple the resistor layer to the electrical therapy circuit as a dump resistor for selectively dumping electrical charge.

3. The implantable medical device of claim 2 wherein the operational circuitry is configured to deliver a high power therapy shock by, at least in part:
    placing the first conductive layer electrically in common with the conductive housing by closing a switch; and
    placing the second conductive layer electrically in common with the ground reference by closing a switch.

4. The implantable medical device of claim 1 wherein the flexible shield comprises a plurality of insulating layers formed of materials selected from the group consisting of polyimide, fluorinated ethylene propylene (FEP), and polyester, or blends thereof.

5. The implantable medical device of claim 4 wherein the plurality of insulating layers comprises a first insulating layer disposed between the first conductive layer and the resistor layer, a second insulating layer disposed between the resistor layer and the second conductive layer, and a third insulating layer covering the second conductive layer, such that the first conductive layer is exposed for contact with the conductive housing.

6. The implantable medical device of claim 4 wherein the plurality of insulating layers comprises a first insulating layer covering the first conductive layer, a second insulating layer between the first conductive layer and the resistor layer, a third insulating layer between the resistor layer and the second conductive layer, and a fourth insulating layer covering the second conductive layer.

7. The implantable medical device of claim 1 wherein the conductive layers comprise copper and the resistor layer comprises a material selected from the group consisting of alloys with nickel and chromium, or alloys with copper and nickel.

8. The implantable medical device of claim 1 further comprising a high power capacitor for use by the electrical therapy circuit, the high power capacitor being separated from the conductive canister by the shield.

9. The implantable medical device of claim 8 wherein the resistor layer includes patterned regions and blank regions, wherein the patterned regions are shaped and sized such that, when the shield is placed to separate the battery, high power capacitor and operational circuitry from the conductive housing, the patterned regions substantially correspond to the locations of the battery and capacitors, and the blank regions correspond to the operational circuitry.

10. The implantable medical device of claim 9 wherein the patterned regions of the resistor layer comprise an elongated trace of resistive material patterned to curve back and forth across the patterned region to define a resistor having a length and a width.

11. The implantable medical device of claim 1 wherein the resistor layer includes patterned regions and blank regions, wherein the patterned regions are shaped and sized such that, when the shield is placed to separate the battery and operational circuitry from the conductive housing, the patterned regions substantially correspond to the location of the battery.

12. The implantable medical device of claim 1 further comprising a plated through-hole coupled to the resistor layer between the first conductive layer and the second conductive layer.

13. The implantable medical device of claim 12 wherein the plated through-hole coupled to the resistor layer includes a first side and a second side, the first side being closer to the first conductive layer and the second side for placement adjacent the operational circuitry, wherein a first insulating layer covers the first conductive layer and the plated through hole includes a first header on the first side and a second header on the second side, wherein the first conductive layer substantially covers the first header.

14. The implantable medical device of claim 13 wherein the plated through-hole is adjacent an opening in the first insulating layer, the opening formed by laser removal of a portion of the first insulating layer, wherein the laser removal is performed to avoid exposing the header through the first insulating layer.

15. The implantable medical device of claim 1 further comprising a plated through-hole coupled to at least one of the first conductive layer, second conductive layer or the resistor layer, the plated through-hole including a first side and a second side, the first side being closer to the first conductive layer and the second side for placement adjacent the operational circuitry, wherein a first insulating layer covers the first conductive layer and the plated through hole includes a first header on the first side and a second header on the second side, wherein the first conductive layer substantially covers the first header.

16. The implantable medical device of claim 15 wherein the plated through-hole is adjacent an opening in the first insulating layer, the opening formed by laser removal of a portion of the first insulating layer, wherein the laser removal is performed to avoid exposing the header through the first insulating layer.

17. A method of manufacturing an electromagnetic shield for an implantable medical device comprising:
manufacturing a flex circuit comprising at least a first insulation layer, a first non-insulating layer, and a second insulation layer, with the first non-insulating layer disposed between the first and second insulation layers, the flex circuit including a first plated through hole for electrical connection to the first non-insulating layer, the first plated through hole including a first header for disposition on the same side of the first non-insulating layer as the first insulation layer, and a second header for disposition on the same side of the first non-insulating layer as the second insulation layer, the first and second headers and the first plated through hole defining a lumen therethrough, wherein the flex circuit is manufactured such that the first insulation layer includes a portion that covers the first header to close one end of the lumen through the first plated through hole;
applying laser energy through the first plated through-hole lumen to the first insulation layer to substantially remove the portion of the first insulation layer which covers the lumen, while leaving substantially undisturbed a portion of the first insulation layer covering the first header;
wherein the first non-insulating layer is either a conductor layer having substantially conductive properties for providing equipotential connections, or a resistive layer having resistive properties for providing voltage dissipation between two connection points.

18. The method of claim 17, wherein the step of manufacturing the flex circuit includes placing at least a second plated through hole having first and second headers and a lumen therethrough for which the first insulation layer again covers the first header and closes one end of the lumen, wherein the step of applying laser energy also includes substantially removing a portion of the first insulation layer which covers the lumen of the first header of the second plated through hole, while leaving substantially undisturbed a portion of the first insulation layer that covers the first header of the second plated through hole.

19. The method of claim 18 wherein the steps of manufacturing the flex circuit and applying the laser energy are performed to substantially prevent shorting or arcing between the first header of the first plated through hole and the first header of the second plated through hole.

20. A method of manufacturing an implantable medical device (IMD) comprising a battery, capacitors and operational circuitry for the IMD configured for electrical connection with one another, wherein the operational circuitry includes a dump circuit, a ground reference and at least a first high voltage output line; the method comprising:
wrapping a flexible shield around the battery, capacitors and operational circuitry, the flexible shield comprising first and second conductive layers around a resistor layer with a plurality of insulation layers;
electrically coupling the flexible shield to the operational circuitry either before or after the wrapping step, such that the first high voltage output line is coupled to the first conductive layer, the ground reference is coupled to the second conductive layer, and the dump circuit is coupled to the resistor layer;
placing the flexible shield into a conductive housing for the IMD before, between, or after the wrapping and electrically coupling steps;
electrically coupling the conductive housing to at least the first high voltage output line; and
hermetically sealing the conductive housing of the IMD.

* * * * *